US00PP25860P3

(12) United States Plant Patent
Mazzardis

(10) Patent No.: US PP25,860 P3
(45) Date of Patent: Sep. 8, 2015

(54) BLUEBERRY PLANT, 'EB 8-17'

(50) Latin Name: ***Vaccinium* hybrid**
Varietal Denomination: EB 8-17

(71) Applicant: Vincent David Mazzardis, Joondalup (AU)

(72) Inventor: Vincent David Mazzardis, Joondalup (AU)

(73) Assignee: PRUNUS PERSICA PTY LTD, Joondalup (AU)

( * ) Notice: Subject to any disclaimer, the term of this patent is extended or adjusted under 35 U.S.C. 154(b) by 167 days.

(21) Appl. No.: 13/986,861

(22) Filed: Jun. 12, 2013

(65) Prior Publication Data

US 2013/0340129 P1 Dec. 19, 2013

(30) Foreign Application Priority Data

Jun. 14, 2012 (AU) ..... 2012/114

(51) Int. Cl.
*A01H 5/00* (2006.01)
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

(56) References Cited

FOREIGN PATENT DOCUMENTS

AU 2012/114 6/2012

*Primary Examiner* — Annette Para
(74) *Attorney, Agent, or Firm* — Paine Hamblen, LLP

(57) ABSTRACT

A new and distinct variety of blueberry plant, which is denominated varietally hereinafter as 'EB 8-17' and which produces a large fruit, which is mature for harvesting and shipment in the early season under the ecological conditions prevailing in Yanchep, Western Australia.

1 Drawing Sheet

Latin name: '*Vaccinium* Hybrid'.
Varietal denomination: 'EB 8-17'.

RELATED APPLICATION DATA

The present application claims priority from Australian Plant Breeders Rights Application Serial No. 2012/114, and which was filed on 14 Jun. 2012.

BACKGROUND OF THE NEW VARIETY

The present invention relates to a new, novel, and distinct variety of blueberry plant '*Vaccinium* Hybrid', and which has been denominated varietally, hereinafter, as 'EB 8-17'.

ORIGIN AND ASEXUAL REPRODUCTION

The present variety of blueberry plant resulted from an ongoing development program which I've conducted to identify new plant varieties. To this end, I make both controlled and hybrid cross-pollinations in order to produce plant populations from which improved progenies are evaluated and thereafter selected.

The blueberry plant 'EB 8-17' was originated by me, and selected from a population of new plants growing on my farm, which is located near Yanchep Springs, Yanchep, Western Australia. This new variety of plant was developed in 2005 following the controlled cross-pollination of the seed parent 'SB-1' [unpatented] with the pollen parent a blueberry plant named '03-6' [also unpatented]. This first cross-pollination occurred in 2005. The seed parent 'SB-1' is characterized by a blueberry plant that has a semi-upright growth pattern, and which further produces large, firm fruit, with an early season of flowering. In contrast, the pollen parent, blueberry plant '03-6' [unpatented] is characterized by a spreading growth habit, and an early season of flowering and a large fruit size. Seeds derived from this original cross-pollination were removed from the seed parent 'SB-1' and produced approximately 500 plants. These first plants produced a first crop of fruit in 2007. A further assessment of the fruit produced showed desirable fruit qualities, and growth habits. After conducting a further assessment during the 2008 growing season, the new variety 'EB 8-17' was selected as showing particularly desirable traits. Subsequent asexual reproduction of 'EB 8-17', by cuttings, occurred during the 2009 through 2011 growing seasons, and led to the conclusion that the blueberry plant 'EB 8-17' appeared to be distinct, and novel relative to other known blueberry plants. The present variety of blueberry plant is noteworthy for producing extra large and firm fruit, and which further has a small, dry picking scar and an excellent flavor. The new variety further has early flowering and fruit production dates.

BRIEF DESCRIPTION OF THE DRAWINGS

The accompanying drawing, which is provided, is a color photograph of the new blueberry plant variety.

FIG. 1 depicts several whole fruit of the new variety of blueberry plant, including mature fruit displaying an external coloration, which is sufficiently matured for harvesting and shipment, as well as several leaves showing the dorsal and ventral coloration thereof, and a vegetative shoot showing the growth habit of the new variety. The supplied photograph further illustrates a shoot bearing typical leaves, and several of the leaves showing the dorsal and ventral coloration thereof, as well as the fruit produced by the closest known variety of blueberry plant named 'Sharpeblue' [unpatented].

The colors in these photographs are nearly as true as reasonably possible in a color representation of this type. Due to chemical development, processing and printing, the leaves and fruit depicted in these photographs may or may not be accurate when compared to the actual specimen. For this reason, future color references should be made to the color plates as seen in The Royal Horticultural Society Colour Charts ($5^{th}$ Edition), and other common color descriptions provided hereinafter.

NOT A COMMERCIAL WARRANTY

The following detailed description has been prepared to solely comply with the provisions of 35 U.S.C. §112, and does not constitute a commercial warranty (either expressed or implied) that the present variety will, in the future, display the botanical, horticultural or other characteristics as set forth, hereinafter. Therefore, this disclosure may not be relied upon to support any future legal claims including, but not limited to, breach of warranty of merchantability or fitness for any particular purpose, or non-infringement which is directed, in whole, or in part, to the present new variety.

DETAILED DESCRIPTION

Referring more specifically to the botanical and horticultural details of this new and distinct variety of blueberry plant, the following has been observed during the sixth fruiting season, and under the ecological conditions prevailing at the farm of the inventor, which is located near the town of Yanchep Springs, in Yanchep, Western Australia.

PLANT

Plant vigor:
- *Generally*.—Considered strong for the species. This is in contrast to the vigor as expressed by the 'Sharpeblue' blueberry plant where this characteristic is considered only medium to strong.

Plant growth habit:
- *Generally*.—Considered semi-upright. This is in contrast to the growth habit of the 'Sharpeblue' blueberry plant which only has an upright growth habit.
- *Plant size*.—About 1.8 meters in height and about 1.2 meters in width.

One year old shoots:
- *Color*.—Yellow-Green, (RHS 146C).

One year old shoots:
- *Internode length*.—Considered medium to long.

LEAF

Leaf length: Considered medium to long for the species, about 76 mm.

Leaf width: Considered medium to broad for the species, about 42 mm.

Leaf:
- *Ratio of length/width*.—Medium to large for the species.

Leaf shape: Considered ovate.

Leaf color:
- *Dorsal surface*.—Green, (RHS 139A).

Leaf color intensity:
- *Dorsal surface*.—Considered yellow-green (RHS 146B). This is in contrast to the dorsal surface color as displayed by the 'Sharpeblue' blueberry plant where this color is considered light to medium green. This is seen most clearly by reference to FIG. 1.

Leaf:
- *Marginal edge*.—Entire.

FLOWER

Flower bud coloration:
- *Generally*.—A very weak anthocyanin color appears.
- *Open flower color*.—White (RHS NN 155D).

Inflorescence:
- *Length*.—Considered average for the species, about 17 mm.
- *Average flower width*.—About 10 mm.

Flower:
- *Shape*.—The corolla has an urceolate shape.

Flower size:
- *Generally*.—The corolla has a medium size and an average length of 13 mm. This is in contrast to the 'Sharpeblue' blueberry plant where this feature of the flower is considered medium to large.

Corolla tube coloration: Considered to have a very weak to weak anthocyanin coloration. This is in contrast to the same characteristic in the 'Sharpeblue' blueberry plant, which is more predominant, but is still considered weak, overall.

Flower:
- *Ridges*.—Ridges are present on the corolla.

FRUIT

Fruit cluster density:
- *Generally*.—Considered medium for the variety. This is in contrast to the variety most closely similar to it, that being the 'Sharpeblue' blueberry plant [unpatented], and which has a fruit cluster density, which is considered to be dense to very dense.

Unripe fruit color:
- *Intensity*.—Considered yellow-green (RHS 145B). This is in contrast to the unripe fruit color intensity of the fruit produced by the 'Sharpeblue' blueberry plant, which is the closest known variety, and which displays a light to medium green color.

Fruit size:
- *Generally*.—Considered large for the species, about 20 mm. This is in contrast to the fruit produced by the 'Sharpeblue' blueberry plant [unpatented], and which produces fruit which is only medium in size. This can be seen most clearly by reference to FIG. 1.

Fruit shape: When observed in a longitudinal plane, the fruit is oblate in shape.

Sepal orientation: Generally speaking, the sepals are considered semi-erect. This is in contrast to the sepals as displayed in the 'Sharpeblue' blueberry plant where the sepal orientation is considered to be erect.

Sepal form: Incurving. This is in contrast to the sepal form as seen in the 'Sharpeblue' blueberry plant where the sepal form is considered to be straight.

Calyx basin:
- *Diameter*.—Considered medium to large. This is in contrast to the fruit produced by the 'Sharpeblue' blueberry plant where the diameter of the calyx basin is considered small to medium for the variety. The calyx diameter is about 7.3 mm.

Calyx basin depth: Considered very shallow, to average in depth, about 2.2 mm.

Intensity of bloom: Considered average for the species. This is in contrast to the bloom as seen in the 'Sharpeblue' blueberry plant where this same characteristic is considered to be strong.

Fruit skin color: The present color of the skin of the fruit, at full maturity, is considered dark blue-black (RHS 203D).

Fruit firmness: Considered medium to firm. This is in contrast to the fruit produced by the 'Sharpeblue' blueberry plant, which is considered soft to medium for the species.

Fruit sweetness: Considered medium to high for the species. This is in contrast to the fruit sweetness as produced by the 'Sharpeblue' blueberry plant, where the sweetness is considered to be only average for the species.

*Fruit flesh color*.—Yellow-Green (RHS 145D).

Fruit:

*Acidity*.—Considered low to medium for the species. This is lower than the average fruit acidity as experienced with the 'Sharpeblue' blueberry plant, which is the closest known variety.

*Seed color*.—Brown (RHS 200C).

Plant:

*Fruiting type*.—Fruit appears on one year old, and current season shoots.

Vegetative bud burst:

*Generally*.—The vegetative bud burst occurs very early in the season. This is earlier in time than the bud burst as observed for the 'Sharpeblue' blueberry plant under the same ecological conditions.

Flowering on one year old shoots: Generally speaking this date of flowering is quite early in the season, and is earlier in time than the flowering as displayed by the 'Sharpeblue' blueberry plant, which is the closest known variety.

Flowering on current year's shoots:

*Generally*.—Considered very early in the season, and earlier in time than the flowering time as seen on the 'Sharpeblue' blueberry plant, which is the closest known variety.

Date of fruit ripening on one year old shoots: Considered very early in the season, and earlier in time than the fruit ripening as seen on the 'Sharpeblue' blueberry plant, which is the closest known variety, and when grown under similar ecological conditions.

Fruit on current year's shoots: Considered very early, and earlier in time than the fruit ripening date for the 'Sharpeblue' blueberry plant, which is the closest known variety.

Resistance to insects and disease: No particular susceptibilities were noted. The present variety has not been tested to expose or detect any susceptibilities or resistances to any known plant and/or fruit diseases.

Although the new variety of blueberry plant possesses the described characteristics when grown under the ecological conditions prevailing near Yanchep Springs in Yanchep, Western Australia, it should be understood that variations of the usual magnitude and characteristics incident to changes in growing conditions, fertilization, pruning, pest control, frost, climatic variables and horticultural management are to be expected.

Having thus described and illustrated my new variety of blueberry plant, what I claim is new and desire to secure by Plant Letters Patent is:

1. A new and distinct variety of blueberry plant, substantially as illustrated and described, and which is characterized as the novelty by producing a large fruit, which is mature for harvesting and shipment during the early season under the ecological conditions prevailing in Yanchep, Western Australia.

* * * * *

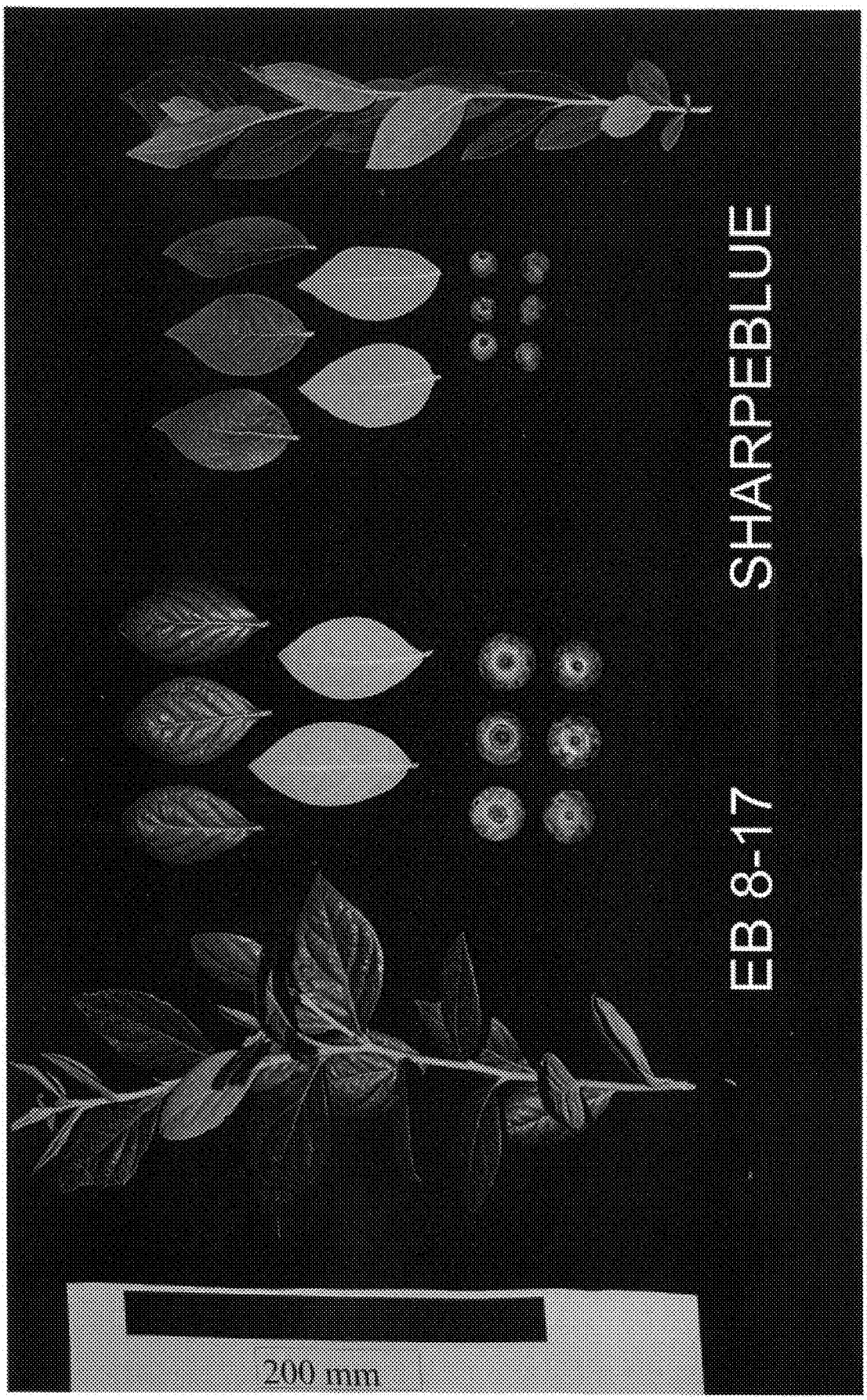
EB 8-17
SHARPEBLUE
200 mm